US00PP34380P2

(12) United States Plant Patent
Klaasse Bos-Bos

(10) Patent No.: US PP34,380 P2
(45) Date of Patent: Jun. 28, 2022

(54) ***ACHILLEA* PLANT NAMED 'BOSACHSKYFI'**

(50) Latin Name: *Achillea millefolium*
Varietal Denomination: Bosachskyfi

(71) Applicant: Adriana Klaasse Bos-Bos, Lijnden (NL)

(72) Inventor: Adriana Klaasse Bos-Bos, Lijnden (NL)

( * ) Notice: Subject to any disclaimer, the term of this patent is extended or adjusted under 35 U.S.C. 154(b) by 0 days.

(21) Appl. No.: 17/499,652

(22) Filed: Oct. 12, 2021

(51) Int. Cl.
*A01H 6/14* (2018.01)
*A01H 5/02* (2018.01)

(52) U.S. Cl.
USPC ..... Plt./263.1

(58) Field of Classification Search
USPC ..... Plt./263.1
See application file for complete search history.

*Primary Examiner* — Annette H Para
(74) *Attorney, Agent, or Firm* — C. Anne Whealy

(57) ABSTRACT

A new and distinct cultivar of *Achillea* plant named 'Bosachskyfi', characterized by its upright and uniform plant habit; vigorous growth habit; freely branching habit; freely flowering habit; inflorescences with red and pale yellow-colored ray florets; and good garden performance.

1 Drawing Sheet

Botanical designation: *Achillea millefolium.*
Cultivar denomination: 'BOSACHSKYFI'.

STATEMENT REGARDING PRIOR DISCLOSURES BY INVENTOR & APPLICANT/ASSIGNEE

An European Community Plant Breeder's Rights application for the instant plant was filed by the Inventor/Applicant on May 4, 2021, application number 2021/1217. Foreign priority is not claimed to this application.

The Inventor/Applicant assert that no publications nor advertisements relating to sales, offers for sale or public distribution occurred more than one year prior to the effective filing date of this application. Any information about the claimed plant would have been obtained from a direct or indirect disclosure from the Inventor/Applicant. Inventor/Applicant claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Achillea* plant, botanically known as *Achillea millefolium*, commonly referred to as Yarrow, and hereinafter referred to by the name 'Bosachskyfi'.

The new *Achillea* plant is a product of a planned breeding program conducted by the Inventor in Aalsmeer, The Netherlands. The objective of the breeding program is to create new vigorous *Achillea* plants with uniform plant habit and large inflorescences with attractive flowers.

The new *Achillea* plant originated from a self-pollination in Aalsmeer, The Netherlands in July, 2016 of a proprietary selection of *Achillea millefolium* identified as code number AB14-000012-015, not patented. The new *Achillea* plant was discovered and selected by the Inventor as a single flowering plant from within the progeny of the stated self-pollination in a controlled greenhouse environment in Aalsmeer, The Netherlands in July, 2017.

Asexual reproduction of the new *Achillea* plant by vegetative tip cuttings in a controlled environment in Aalsmeer, The Netherlands since July, 2017, has shown that the unique features of this new *Achillea* plant are stable and reproduced true to type in successive generations.

SUMMARY OF THE INVENTION

Plants of the new *Achillea* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Bosachskyfi'. These characteristics in combination distinguish 'Bosachskyfi' as a new and distinct *Achillea* plant:

1. Upright and uniform plant habit.
2. Vigorous growth habit.
3. Freely branching habit.
4. Freely flowering habit.
5. Inflorescences with red and pale yellow-colored ray florets.
6. Good garden performance.

Plants of the new *Achillea* differ from plants of the parent selection in ray floret color as plants of the new *Achillea* have red and pale yellow-colored ray florets whereas plants of the parent have light pink-colored ray florets. In addition, plants of the new *Achillea* are more compact than plants of the parent selection.

Plants of the new *Achillea* can also be compared to plants of *Achillea millefolium* 'Desert Eve Cream', not patented. In side-by-side comparisons, plants of the new *Achillea* differ primarily from plants of 'Desert Eve Cream' in ray floret color as plants of the new *Achillea* have red and pale yellow-colored ray florets whereas plants of 'Desert Eve Cream' have cream-colored ray florets. In addition, plants of the new *Achillea* are larger than and not as compact as plants of 'Desert Eve Cream'.

BRIEF DESCRIPTION OF THE PHOTOGRAPH

The accompanying photograph illustrates the overall appearance of the new *Achillea* plant showing the colors as true as it is reasonably possible to obtain in colored reproductions of this type. Colors in the photograph may differ slightly from the color values cited in the detailed botanical description which accurately describe the colors of the new *Achillea* plant. The photograph is a top perspective view of a typical flowering plant of 'Bosachskyfi' grown in a container.

DETAILED BOTANICAL DESCRIPTION

The aforementioned photograph and following observations and measurements describe plants grown during the late summer in 17-cm containers in an outdoor nursery in Aalsmeer, The Netherlands and under cultural practices typical of commercial *Achillea* production. During the production of the plants, average daily temperatures were 22° C. and average night temperatures were 17° C. Plants were 25 weeks old when the photograph and description were taken. In the following description, color references are made to The Royal Horticultural Society Colour Chart, Second Edition, except where general terms of ordinary dictionary significance are used.

Botanical classification: *Achillea millefolium* 'Bosachskyfi'.

Parentage: Self-propagation of a proprietary selection of *Achillea millefolium* identified as AB14-000012-015, not patented.

Propagation:

- *Type*.—Terminal vegetative cuttings.
- *Time to initiate roots, summer*.—About 16 days at temperatures about 26° C.
- *Time to initiate roots, winter*.—About three weeks at temperatures about 23° C.
- *Time to produce a rooted cutting, summer*.—About 24 days at temperatures about 23° C.
- *Time to produce a rooted cutting, winter*.—About four weeks at temperatures about 18° C.
- *Root description*.—Medium in thickness, fibrous; typically white to light yellow in color, actual color of the roots is dependent on substrate composition, water quality, fertilizer type and formulation, substrate temperature and physiological age of roots.
- *Rooting habit*.—Moderately freely branching habit; medium density.

Plant description:

- *Plant and growth habit*.—Perennial plant appropriate as a container or garden plant; upright and uniform plant habit; vigorous growth habit; moderate growth rate; freely basal branching habit with about twelve primary branches each with about six secondary lateral branches developing per plant.
- *Plant height*.—About 50 cm.
- *Plant diameter or spread*.—About 64 cm.
- *Lateral branches*.—Length: About 49 cm. Diameter: About 5 mm. Internode length: About 4 cm. Aspect: Upright to about 45° from vertical. Strength: Strong. Texture and luster: Pubescent; glossy. Color, developing: Close to 142B. Color, developed: Close to 143C.

Leaf description:

- *Arrangement*.—Alternate, simple; sessile.
- *Length*.—About 2 cm.
- *Width*.—About 1 cm.
- *Shape*.—Overall, oblong; feathery and fern-like.
- *Apex*.—Acute.
- *Base*.—Cuneate.
- *Margin*.—Deeply and finely dissected, pinnatisect; lobes divergent.
- *Texture and luster, upper and lower surfaces*.—Pubescent; glossy.
- *Venation pattern*.—Pinnate.
- *Color*.—Developing leaves, upper and lower surfaces: Close to 143A. Fully expanded leaves, upper and lower surfaces: Close to 143A; venation, close to 143C.

Inflorescence description:

- *Arrangement and habit*.—Rotate composite inflorescence form; inflorescences arranged in terminal or axillary compound corymbs; corymbs are mostly flat-topped to slightly rounded; freely flowering habit with about 264 inflorescences per terminal corymb with numerous corymbs developing per plant; corymbs positioned above the foliar plane and face mostly upright.
- *Fragrance*.—Noticeable; pleasant.
- *Time to flower*.—Plants flower during June and July in The Netherlands; inflorescences not persistent.
- *Inflorescence buds*.—Height: About 5 mm. Diameter: About 3 mm. Shape: Ovoid. Texture and luster: Pubescent; glossy. Color: Close to 145A.
- *Corymb diameter*.—About 9 cm.
- *Corymb height*.—About 7 cm.
- *Inflorescence diameter*.—About 8 mm.
- *Inflorescence height*.—About 7 mm.
- *Disc diameter*.—About 4 mm.
- *Receptacle diameter*.—About 2 mm.
- *Receptacle height*.—About 1 mm.
- *Receptacle shape*.—Rounded, button-shaped.
- *Receptacle color*.—Close to 143A.
- *Ray florets*.—Quantity and arrangement: About five in a single whorl; ray florets face outwardly. Length: About 3 mm. Width: About 4 mm. Shape: Elliptic. Apex: Obtuse with truncate tendencies; undulate. Base: Obtuse. Margin: Entire; slightly undulate. Texture and luster, upper and lower surfaces: Smooth, glabrous; matte. Color: When opening, upper surface: Close to 46A. When opening, lower surface: Close to 53D; proximally close to 19C. Fully opened, upper surface: Close to 53A; venation, close to 53A; with subsequent development, color becoming closer to 53B and 53C; proximally close to 19C. Fully opened, lower surface: Close to 53D; proximally close to 19C; venation, close to 53D and 19C; with subsequent development, color becoming closer to 19C.
- *Disc florets*.—Quantity and arrangement: About 16 massed at the center of the receptacle. Length: About 4 mm. Diameter: About 1 mm. Shape: Tubular; apex, five-pointed. Texture and luster; upper and lower surfaces: Smooth, glabrous; matte. Color, upper and lower surfaces: Close to 5A.
- *Phyllaries*.—Quantity and arrangement: About 15 arranged in about three whorls; imbricate and tightly appressed to the ray florets. Length: About 4 mm.

Width: About 2 mm. Shape: Elliptic. Apex: Acute. Base: Cuneate. Margin: Entire. Texture and luster, upper surface: Pubescent; glossy. Texture and luster, lower surface: Smooth, glabrous; glossy. Color, upper and lower surfaces: Close to 143A.

*Peduncles*.—Length, terminal peduncle: About 6 mm. Diameter, terminal peduncle: About 1 mm. Length, third peduncle: About 2 cm. Diameter, third peduncle: About 1 mm. Strength: Moderately strong. Aspect: About 45° from vertical. Texture and luster: Pubescent; glossy. Color: Close to 143B.

*Pedicels*.—Length: About 5 mm. Diameter: About 1 mm. Strength: Flexible. Aspect: Erect to about 30° from vertical. Texture and luster: Pubescent; glossy. Color: Close to 143A.

*Reproductive organs*.—Androecium (present on disc florets only): Quantity: About five. Filament length: About 1 mm. Filament color: Close to 143C. Anther shape: Narrowly oblong; basifixed. Anther size: About 0.1 mm by 1 mm. Anther color: Close to 1A. Pollen amount: Abundant. Pollen color: Close to 17A. Gynoecium (present on disc and ray florets): Quantity: One. Pistil length: About 3 mm. Stigma diameter: About 1 mm. Stigma shape: Bi-parted. Stigma color: Close to 150C. Style length: About 2 mm. Style color: Close to 145A. Ovary color: Close to 157A.

*Seeds and fruits*.—To date, seed and fruit production has not been observed on plants of the new *Achillea*.

Pathogen & pest resistance: To date, plants of the new *Achillea* have not been shown to be resistant to pathogens and pests common to *Achillea* plants.

Garden performance: Plants of the new *Achillea* have been observed to have good garden performance and tolerate wind, rain and to tolerate temperatures ranging from about −37° C. to about 35° C. and to be suitable for U.S.D.A. Hardiness Zone 3.

It is claimed:

1. A new and distinct *Achillea* plant named 'Bosachskyfi' as illustrated and described.

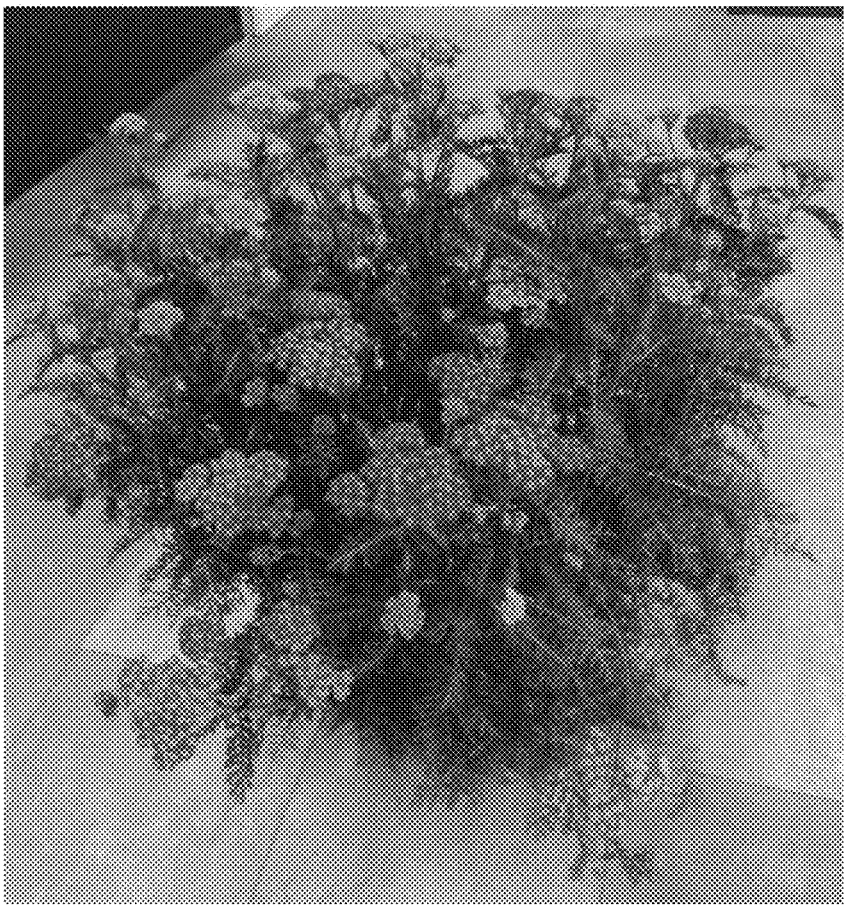

* * * * *